(12) United States Patent
Cyrulnik

(10) Patent No.: US 7,409,040 B2
(45) Date of Patent: Aug. 5, 2008

(54) SYSTEM AND METHOD FOR NONINVASIVE DIAGNOSTIC IMAGING, DETECTION, AND IDENTIFICATION OF SUBSTANCES BY MICROWAVE/RF MODULATION OF X-RAYS AND APPLICATIONS IN TREATMENT OF DISEASES CHARACTERIZED BY THE PRESENCE OF PATHOLOGICAL MACROMOLECULES OR BY THE NEED FOR REGENERATION OF NORMAL TISSUE

(76) Inventor: Reuven Avrohom Cyrulnik, 639 Marshall Pl., Long Beach, CA (US) 90807

( * ) Notice: Subject to any disclaimer, the term of this patent is extended or adjusted under 35 U.S.C. 154(b) by 110 days.

(21) Appl. No.: 10/519,305

(22) PCT Filed: Jun. 20, 2003

(86) PCT No.: PCT/US03/19410

§ 371 (c)(1),
(2), (4) Date: Jul. 11, 2005

(87) PCT Pub. No.: WO04/000414

PCT Pub. Date: Dec. 31, 2003

(65) Prior Publication Data

US 2005/0245818 A1    Nov. 3, 2005

Related U.S. Application Data

(60) Provisional application No. 60/391,351, filed on Jun. 25, 2002, provisional application No. 60/390,995, filed on Jun. 24, 2002, provisional application No. 60/390,768, filed on Jun. 21, 2002.

(51) Int. Cl.
*A61N 5/10* (2006.01)
(52) U.S. Cl. .......................................... 378/65; 378/53

(58) Field of Classification Search .................. 378/65, 378/53
See application file for complete search history.

(56) References Cited

U.S. PATENT DOCUMENTS

| 5,044,006 A | 8/1991 | Cyrulnik |
| 5,578,709 A | 11/1996 | Woiszwillo |
| 6,310,352 B1 | 10/2001 | Gross et al. |

OTHER PUBLICATIONS

Datta, JI. American Medical Association 271:800('94). [Microwaves with x-rays to treat malignant brain tumors.].
Beardsley, T.A. A War Not Won. Scientific American Jan. '94:130 [Lack of significant improvement in overall cancer demise rate].

(Continued)

*Primary Examiner*—Chih-Cheng G Kao
(74) *Attorney, Agent, or Firm*—Katten Muchin Rosenman LLP

(57) ABSTRACT

A modulated x-ray system and method provide various applications to increase medical diagnoses and treatment as well as non-medical scenarios. At low energy levels, it is used as a sophisticated medical diagnosis tool, localizing and imaging a variety of biological systems and conditions for further characterization, rather than for destruction. As a therapeutic device, it is used for directed treatment of infectious diseases, treatment of general medical diseases such as atherosclerosis and autoimmune diseases, and genetic therapy. In one embodiment, eliminating unwanted tissue anywhere in the body, effectively allows non-invasive surgery. In another embodiment, selective destruction/activation of specific cells allows for regeneration of cells and tissues, such as spinal cord regeneration.

27 Claims, 5 Drawing Sheets

OTHER PUBLICATIONS

Webb, S. & Booth A. Absorption of Microwaves by Microorganisms. Nature 222:1199-1200 ('69) [Frequency selective-DNA].

Webb, S.J. Effects of Microwaves on Normal and Tumor Cells as Seen by Laser-Raman Spectroscopy. J. Microwave Power 11:138 '76.

Grundler, W. and Keilman, F. Physical Review Letters. 51:1214 '83 [Strong frequency dependence on yeast prove nonthermal resonant microwave sensitivity in biology.].

Gandhi, o. Ed. Biological Effects and Medical Applications of Electromagnetic Energy. pp. 380-382. '90. Frequency Specific Effects.

Mickey, G.H. Electromagnetism and its Effect on the Organism. NY State J. Medecine 63:1935-42 ('63). [Frequency specific killing of viruses without affecting the host; chromosomal mutation].

West, B. and Regelson, W. Pulsed Radio Wave Effects on Tumor Growth, J. Microwave Power 11:176-7 ('76).

Baranski, S. and Czersk, Biological Effects of Microwaves. 70-71, 132-4 '76. Chromosomal Effects. Possible Genetic Effects and Influence of Microwave Radiation on Mitosis. Cellular Effects.

Klainer, S. and Frazer, J. Raman Spectroscoopy of Molecular Species During Exposure to 100 MHz Radio-Frequency Fields. Ann NY ACAD Sci. 323-6 ('74) [Frequency effects on T-RNA].

Frohlich, H. The Biological Effects of Microwaves. Adv. Electron and Electron Physics 53:127-50 ('80) [Frequency specific effects on bacteria, yeast, viruses, protein metabolism, bone marrow, and Raman spectral absorption.].

Revzin, A. and Neumann, E. Conformation Changes in R-RNA Induced by [1 MHz] Electric Impulses. Biophys. Chem. 2:144-50 ('74).

Averbeck, D. Et al. Microwave [inter] Action in Cells With X-ray. J. Microwave Power 11:143 ('76).

Varma, M. and Raboulay. DNA Studies in Measuring Mutagenicity Caused by Non-Ionizing Radiation. Mutation Res: 31:386-92 ('75).

Greenebaum, V. et al. Long-Term Effects of Weak 45-75 HZ EM Fields on the Slime Mold. Technical Report, U. wisconsin ('75).

Mittler, S. Non-Thermal Radiowaves and Genetic Damage in *Drosophila*, Proc. IEEE, 6th Annual Meeting, Miami Beach.

Luczak, M. et al. Effect of Microwaves on Virus Multiplication in Mammalian Cells J. Microwave Power 11:173-4 ('76).

Webb, S. and Dodds, D. Inhibition of Bacterial Cell Growth by 136 GC Microwaves, Nature 218:374-5 ('68).

Glaser, Z.R. Biomedical Aspeccts of Radio Frequency and Microwave Radiation. Science Policy Research Division, Lib. Congress.

Sevastyanova, L. and Potapov. Resonance Effect in Biological Action of Microwave Radiation. IEEF Symposium, ('76).

Schliepake, Erwin, The Medical Use of Electrical high Frequencies. English Translation of 2nd German Edition by R. King Brown, Actinic Press, London: '35.

Karzmark, C.J. Adavances in Linear Accelerator Design for Radiotherapy, Medical Physics 11:2, 105-128, '84.

SYSTEM AND METHOD FOR NONINVASIVE DIAGNOSTIC IMAGING, DETECTION, AND IDENTIFICATION OF SUBSTANCES BY MICROWAVE/RF MODULATION OF X-RAYS AND APPLICATIONS IN TREATMENT OF DISEASES CHARACTERIZED BY THE PRESENCE OF PATHOLOGICAL MACROMOLECULES OR BY THE NEED FOR REGENERATION OF NORMAL TISSUE

RELATED APPLICATIONS

This application is the National Stage of International Application No. PCT/US2003/019410, filed Jun. 20, 2003, which claims the benefit under 35 U.S.C. 119(e) of U.S. Ser. No. 60/390,768 filed Jun. 21, 2002, U.S. Ser. No. 60/390,995 filed Jun. 24, 2002 and U.S. Ser. No. 60/391,351 filed Jun. 25, 2002 which is herein incorporated by reference.

BACKGROUND OF THE INVENTION

1. Field of Invention

The present invention relates generally to the field of radiotherapy treatment systems. More specifically, the present invention is related to application of modulated x-rays.

2. Discussion of Prior Art

U.S. Pat. No. 5,044,006, entitled MICROWAVE FREQUENCY MODULATION OF X-RAY BEAM FOR RADIO THERAPY TREATMENT SYSTEM, commonly invented (Cyrulnik), issued on Aug. 27, 1991, and hereby incorporated by reference, discloses a method and apparatus for producing an x-ray beam modulated at a microwave frequency for absorption by pathological materials including macromolecules, such as oncogenes, for the radiological therapeutic treatment of tumors and other pathological conditions. As disclosed by Cyrulnik, the atomic structure of certain macromolecules (molecules having a backbone structure of 20,000 or more atoms) suggests that such molecules may have a "signature" frequency for resonant energy absorption. In the system of Cyrulnik, an x-ray beam is amplitude modulated at a predetermined or empirically determined microwave frequency equal to a resonant interactive frequency for a selected pathological material. Sufficient x-ray energy may be supplied, for example, in order to destroy the pathological material.

The teachings of the U.S. Pat. No. 5,044,006 patent are best understood with the following discussion of the technology in conjunction with original FIGS. 2 and 6 of the '006 patent (herein FIGS. 1 and 2):

1. Molecular Orbitals

The energy of an electron in orbit must be sufficient to counterbalance the attracting electromagnetic force maintaining it in orbit, which, like gravitational force, varies inversely with the square of its distance to the center of attraction, that is, the size of the orbit. The energy absorbed in a transition between adjacent orbitals therefore varies inversely with the difference in the squares of these distances, which are close to each other in value being adjacent:

$$a^2 - b^2 = (a-b)(a+b)$$

which approximates a constant×a, so that the energy absorbed is inversely proportional to the size of the orbital.

2. DNA

Deoxyribonucleic acid, the genetic material of which the chromosomes of human cells are composed, consists of pairs of macromolecules containing a backbone of units of 5 carbon atoms linked by phosphorous and oxygen atoms and each with a side chain of a purine or pyrimidine base. Viruses and genes that cause cancer (oncogenes) consist of such macromolecules with lengths on the order of 4,000 base pairs, or a backbone of some 20,000 atoms.

3. Resonant Frequency

The lowest transitions of electron orbitals in single atoms result in absorption of visible light, which has a frequency about $4(10^{14})$ cycles per second (cps). As previously explained, and as can be shown rigorously, the frequency of absorption by the lowest transition of molecular orbitals varies inversely with the size of the molecule.

A molecule 20,000 base pairs in length, each containing a string of 8 atoms per set of exons and introns, would therefore be expected to absorb radiation at a frequency of:

$$[1/(8 \cdot 2)](1/2 \cdot 10^4)(4 \cdot 10^{14}) = 4/32 \cdot 10^{10} = 1.25 \cdot 10^9 \text{ cps}$$

which is in the microwave range.

4. Penetration by Modulation

The principle used extensively in radio and television transmission of modulating a carrier wave by one of considerable different frequency can be utilized to overcome the difficulty of delivering selectively-absorbable radiation with destructive potential to oncogenes. When the carrier wave is modulated by a signal containing a square wave component such as occurs when it is generated by a device that is turned on and off at the modulating frequency, then radiation with components at both frequencies results, so that resonant absorption of the compound carrier wave can take place. In this way, if an x-ray beam is turned on and off at a resonant microwave frequency, it can act as a carrier wave to allow penetration of the microwave frequency energy to its otherwise inaccessible target, and at the same time be selectively absorbed by macromolecules such as oncogenes whose resonant frequency of absorption is tuned to the frequency of modulation of the x-ray beam by the microwave frequency.

This can be accomplished by interposing a klystron or similar device in the high voltage circuit of the x-ray generating tube, which will turn the beam on and off at microwave frequencies.

5. Detection

To determine when absorption is occurring and by which structures without having to empirically destroy tissue by trial and error, modulate the x-ray beam of a CAT scanner with a klystron or similar device. A CAT scanner detects the absorption of a standard low radiation level diagnostic x-ray beam at any point inside the body by dividing that beam so that it is viewed from several angles.

If this is done over the spectrum of frequencies of possible absorption by oncogenes, then at those frequencies which are absorbed by the genetic material unique to the tumor or malignancy, that tissue, and that tissue alone, will show up as absorbent on the scan.

The spectrum of microwave frequencies can be impressed on the scanner's x-ray beam at each angle during the course of a single scan by systematically varying the klystron frequency. Since absorption occurs in $10^{-9}$ seconds, the electron beam, which has a single target dwell time of 100 microseconds, can accommodate $10^{-4}/10^{-9} = 10^5$ different microwave frequencies of modulation. Thus, each of the 30,000 or so human genes could be tested for unique absorption at 3 frequencies in one scan, allowing for allelic mutation.

A scan would be generated from memory for each frequency by sampling the detector output at any particular time delay after the initiation of the beam. Each absorbing structure, such a tumor, would "light up" when its resonant frequency is selected.

Although only a small portion of the x-ray beam is utilized at any given modulating frequency, this is sufficient to produce the same intensity of absorption as is seen on an ordinary CAT scan, as will be shown in the next section.

6. Safety

In an ordinary plain skull x-ray series (which contains the same dose of radiation as a CT scan), approximately 3% of the x-ray beam is absorbed in total, of which the brain absorbs 1%. This $3/10,000$ of the beam is absorbed by a column of cells given by the cube root of the number of cells in the roughly spherical brain, which total $3(10^{10})$, their cube root being about 3000.

If, instead of the type of absorption seen in a spectrophotometer where each subsequent unit absorbs the same proportion of the beam, the entire beam is absorbed by a single cell, then in order to absorb the same amount of radiation as in an ordinary CT scan (and thus in an ordinary skull x-ray), a single cell would have to absorb $1/3000$ of the $3/10,000$ of the beam which is $1/10^7$. The duty cycle of modulation limits to this maximum the absorbable radiation at each frequency of modulation of the x-ray beam during imaging.

Therefore, even though each resonant cell absorbs the entire available beam at that frequency, it absorbs no more than would be absorbed from an ordinary plain film, yet it absorbs 3000 times as much as other cells and 30 times as much as bone, allowing safe but effective detection by CT.

7. Treatment

Once the unique frequency of absorption of the modulated x-ray beam has been determined as noted above, selective destruction of undesirable structures such as oncogenes or their RNA transcripts, viruses, or other macromolecular nucleic acid configurations can be accomplished by scanning the patient a second time, this time with the klystron tuned to the unique resonant frequency of absorption throughout the duration of the x-ray beam. In this way the duty cycle during absorption is increased by a factor of approximately $10^9$. (Before, it was turned on $10^9$ times per second, each time at a different frequency; now each of the $10^9$ times occurs at the single unique resonant absorbed frequency). Even if every cell of one of the several cell types in the brain were malignant, the increased dosage at full duty cycle of a factor of $10^9$ of radiation specifically to those cells, each absorbing 3000 times the radiation that it would in a conventional skull x-ray series or Cr scan, would be sufficient to eliminate or deimmortalize them all. In practice, a tumor becomes symptomatic at a cell volume of approximately $10^5$ cells, so that the effective dosage delivered to such a tumor would be equivalent to $3000(10^9)(10^{-5})=3(10^7)$ rads per cell (the total radiation dose in a CAT scan being on the order of a rad), which is 3000 times the curative maximum dosage used in radiotherapy, with the significant difference being that in this case the dosage delivered to the rest (nonmalignant) of the cells which do not absorb is still only one additional rad for this second scan, so that the treatment would be safe to normal cells.

In conventional radiation therapy, however, lethal tumor dose of 5000 rads represents a total, each cell only absorbing $1/10^5$ of this (or, in the case of neoplastic cells a somewhat greater multiple of the same order of magnitude) i.e. about $1/10$ of a rad. With the proposed technique, this can be multiplied $10^5$ fold, which would easily destroy the tumor, even if repair is allowed for. Fractionation of the 5000 rads into 200 rad doses to minimize radiation damage to other tissues can be obviated, minimizing repair of the tumor cells.

The net lethal effect on target tissue of the proposed technique is on the order of 100 times that of conventional radiotherapy, whereas radiation exposure of nontargeted tissue is 3000 times less than a diagnostic x-ray series.

Of course, with the disclosed technique the dose can also be fractionated by reducing the duty cycle if 100 times the lethal tumor dose is not needed, depending on the clinical situation such as the size of the tumor. Higher doses can also be achieved if desired by repeating the scan at full duty cycle, each repetition doubling the dose to the malignancy with negligible additional radiation to healthy tissue. Furthermore, once the unique frequency of resonant absorption is determined using the CT scanner, the klystron or other modulating device can be connected to conventional x-ray equipment, whether a simple diagnostic x-ray tube or radiotherapy equipment, in order to modulate its beam so as to achieve a more rapid treatment session than with a CAT scanner.

It should be noted that, unlike other techniques which selectively target tissue in a spatial manner by limiting radiation to a small area at the site of the tumor, the disclosed technique, though highly selective against undesirable tissue, is not limited in space, and can thus destroy those malignant cells outside the main tumor bulk which are responsible for recurrence, failed surgery, and metastasis. In principle, I.Y.H. this technique could be used in a total body fashion to cure metastatic malignancy because of its high selectivity and consequent high safety factor and effectiveness.

Furthermore, since the detection process is empirical, determining solely which frequency is uniquely absorbed by the malignancy, it does not depend on the cause(s) of cancer; as long as there is an abnormal genetic configuration unique to the tumor, even if it also involves loss of inhibition by an inactivated or abnormally absent gene, the change in that length of the DNA molecule being transcribed by the chromosome should result in a unique pattern of absorption with consequent destruction of the tumor by the radiation.

8. Equipment

Disclosed is the concept of producing selective elimination of undesirable entities by achieving resonant absorption of penetrating radiation by their macromolecules of specific configuration, such as oncogenes and viruses, by means of modulation of the radiation at that resonant frequency whose unique absorption is determined in a safe manner using computerized tomography (CT). The method of achieving unique absorption of high energy radiation by modulating at the resonant frequency was an innovation in this proposal, as is its application in the treatment of malignancy, including determining, in a unique manner, the frequency of modulation resulting in absorption empirically but safely using CT.

The equipment itself consists of a CT scanner and a klystron microwave device, both of established safety and effectiveness. Guidelines for use have also been established including shielding requirements. (The current proposal would not change the penetrating characteristics of the radiation, so that these operating characteristics would still pertain, in particular as regards shielding, which again, are well established.) As the above analysis shows, the proposed combination of these devices exhibits enhanced effectiveness at no cost to safety.

FIG. 1 (FIG. 1 of '006 patent) shows a radiating system 20 including a CT scanner 22 which has been modified, as will be described below. The scanner 22 includes a plurality of x-ray sources 24, of which three are shown by way of example, and a plurality of x-ray detectors 26, of which three are shown by way of example. The sources 24 and the detectors 26 are held in their respective positions by a frame 28 which encircles a subject 30 which is typically a living creature such as a human being or an animal. The sources 24 and the detectors 26 are positioned symmetrically about the subject 30, and are connected electrically to a controller 32 which includes circuitry. In particular, it is noted that each of the sources 24 is connected by two electric lines to the controller 32, a first of the lines 34 providing an electric signal which activates the source 24, and a second of the electric lines 36 providing an electric signal which modulates the x-ray beam at a predetermined modulation frequency. The detectors 26 are connected by electric lines 38 to the controller 32 for inputting data about detected radiation to the controller 32.

FIG. 2 (FIG. 2 of '006 patent) shows details in the construction of one of the sources 24, as well as components of the controller 32, and an interconnection between the controller 32 and one of the detectors 26. All of the sources 24 function in the same manner, and all of the detectors 26 function in the same manner. The x-ray source 24 comprises a target 40 rotated by a motor 42, and a collimator 44. The collimator is positioned along a path of x-rays emanating from the target 40 for defining an x-ray beam 46 directed towards the subject 30. The source 24 further comprises an electron gun 48 which includes a filament 50 and an electrode assembly 52. The filament 50 is used to emit electrons which are accelerated by electric potentials on the electrode assembly 52 and the target 40 relative to the filament 50, the accelerated electrons forming a beam 54. Electrons of the beam 54 strike the target 40 to generate the x-rays, the process of generation of the x-rays being well-known. A battery 56 connected between the target 40 and the filament 50 symbolically illustrates electric potential in the range of thousands of volts applied between the target 40 and the filaments 50. Electric potential for the electrode assembly 52 is provided from a bias voltage source 58 within the controller 32, the voltage of the source 58 being coupled to the electrode assembly 52 via a switch 60 also located within the controller 32.

The x-ray source 24 further comprises a klystron 62 of which two cavities 64 and 66 are shown in longitudinal sectional view, the cavity 64 being located between the cavity 66 and the electrode assembly 52. The central axis of the klystron 62 coincides with an axis of the electron beam 54. The beam 54 passes through an aperture 68 in an end wall 70 of the cavity 64, a tubular region 72 interconnecting the cavities 64 and 66, and an aperture 74 in an end wall 76 of the cavity 66. A probe 78 in the form of a loop is located in the cavity 64 for receiving inputted microwave power. Microwave power is provided by way of a microwave signal generated within a microwave source 80 located within the controller 32, the microwave signal being coupled from the source 80 to the probe 78 via a switch 82 also located within the controller 32.

Also included within the controller 32 is a computer 84, a frequency selector 86, an analog-to-digital converter 88 and a switch 90. Signals from a detector 26 are coupled by the switch 90 to the converter 88, the converter 88 converting the analog signals of the detector to digitally formatted signals to be inputted to the computer 84.

FIG. 3 (FIG. 6 of the '006 patent) illustrates a basic radiotherapy method. The procedure begins with a modulation of the x-ray beam with the microwave signal. The beam is directed upon the subject and the microwave modulating signal is swept in frequency. The radiation propagating from the x-ray source and through the subject is detected. This is followed by a recording of the frequencies at which absorption of radiant energy occurs. After this information has been obtained, the x-ray beam is modulated at a specific frequency for which absorption has been noted. Then, the beam while modulated at the specific absorption, or resonant, frequency is directed at the subject for irradiating the subject. Photon energy is transferred to macromolecules within the subject for destruction of the macromolecules. Where the macromolecules represent a malignancy, the procedure of the invention destroys the malignancy without damaging neighboring tissue.

The following prior art describe known initial therapeutic achievements and frequency specific biological effects of microwaves 1. Frequency Specific Absorption by DNA, RNA, Protein and Invivo Webb and Booth[3] performed microwave spectroscopy on DNA, RNA, protein, and bacteria, showing individual frequency-specific absorption peaks for each substance which correspond to those of intact cells, with the intensity of absorption at each peak being proportional to the relative proportion of those substances in the cell.

Furthermore, there were frequency specific effects on growth rate of the cells, all corresponding with absorption peaks in the spectra (those of DNA inhibiting growth, those of RNA at one peak inhibiting and at one stimulating growth).

In a review for the Naval Research Institute, Glaser and Dodge[19] reported that microwaves between 40 and 150 GHz were found to selectively interfere with the synthesis of DNA and protein, and that the effect appeared to be frequency dependent. Lower frequencies did not show nonthermal mutagenic effects.

2. Differential Absorption by Tumors at Specific Frequencies

Webb[4], using laser-Raman spectroscopy, demonstrated that tumor cells absorb microwaves at specific frequencies not absorbed by normal cells and could selectively alter the metabolism of tumor cells in a nonthermal manner by exposure to frequencies harmless to normal cells, all effects being frequency specific.

3. Narrow Resonant Effects of Microwaves on Growth of Cells

Grundler and Keilmann[5] found that microwaves influence the growth of yeast with a surprisingly strong frequency dependence, with resonance as narrow as 8 megahertz, confirming the existence of a non-thermal resonant microwave sensitivity in cells. The sharp frequency dependence and effect at low intensity of radiation are indicative of a nonthermal action[6]. Webb and Dodds[18] also detected decreased growth of E. Coli with 136 GCmicrowaves.

4. Frequency Specific Genetic and Viral Destruction

Mickey and colleagues[7] demonstrated non-thermal biological effects of high frequency radio waves, including frequency-specific killing of viruses and microorganisms without affecting the host, genetic changes at specific loci, chomosomal aberrations, lethal mutations, and frequency specific denaturation.

A Soviet study[20] using millimeter waves was reported to show maximal effect pealing at 6.5 MM., resulting in decreased viral infective activity, increased phage activity. Cell wall disruption, protoplasmic degeneration, altered red blood cell stability, altered nucleic acid and protein concentration, and effects on hematopoiesis and liver cell nuclei and mitochondria.

Viral multiplication in mammalian cells was affected by microwaves as a result of changes in nucleic acid and protein synthesis, resulting in lowered multiplication of herpes virus in infected cells, as reported by Luczak, et al[17].

5. Selective Destruction of Tumor by Microwaves

West and Regelson[8] noted reduction in tumor size and significantly reduced viability of lung tumor cells and leukemia cells with no lethality of normal embryo cells at low levels of pulsed nonthermal irradiation at 27.12 MHz.

6. Specific Microwave Effects on Chromosomes and DNA

Baranski and Czersk[9] noted chromosomal effects and influence of microwave radiation on mitosis, with depressed cell proliferation and chromosomal despirilization, a picture never seen in ionizing radiation induced damage. They felt this indicated with high probability that molecular effects that influence the spatial structure, energy levels, and consequently, the biological and metabolic activity of macromolecules are responsible for these effects in contrast to electrical field changes. Optical Density studies by Varma and Traboulay[14] showed DNA strand separation in the GHz range of microwave non-ionizing radiation.

Together, these studies indicate that the frequencies of resonant absorption decrease with increasing molecular size, 100 MHz affecting T-RNA, while millimeter waves affect macromolecular proteins, for example. Similar effects were noted by Revzin and Neumann[12], who detected conformation changes in ribosomal-RNA using pulsed MHz radiation, with changes in orientation of the entire RNA molecule concomitant with helix coil transitions of oligomeric base-pair regions, suggesting restructuring of units the size of genes or their transcripts.

7. Mechanism of Action of Microwaves on DNA

Considering the interaction of electromagnetic energy with living systems in the light of quantum effects, Baranski and Czersk note that if the photon energy of irradiation corresponds to quantum differences among the various possible energetic states of a molecule, a quantum of energy may be absorbed and excitation of the molecule occurs. Return to the unexcited state may take place by energy transfer by rearrangements within the molecule. Thus, fluctuations from the equilibrium distribution of tertiary structure (e.g. denaturation) are expected.

8. Enhanced Effect of X-Rays Combined with Microwaves

Averbach, et al[13], observed decreased growth of *E. Coli* bacteria at specific microwave frequencies of 70.5 and 73 GHz and reported on a possible interaction with X-rays.

Mickey and Colleagues[7] showed that microwave-range waves acting in conjunction with Gamma rays are far more mutagenic than either type of radiation alone.

Frequency specific effects of microwave radiation have been described by Kainer and Frazer[10] by Raman spectroscopy, and in a review by Frolich[11] describing resonant effects on growth of bacteria, yeast, viruses, protein, metabolism, and alterations in the effects of x-rays on bone marrow.

9. Some Characteristics of the Glutathione Cycle Revealed by Ionizing and Non-Ionizing Electromagnetic Radiation Holt J A, Med Hypotheses 1995 October; 45(4):345-68 Microwave Therapy Centre, West Perth, Australia.

The cyclic reaction of GSH-->GSSG-->GSH (designated R(exp) or R(e)) obeys the three specific features of life by producing energy in exponential quantities relative to time, is in effect irreversible and is inherited from generation to generation. In multicellular life, this reaction produces the energy for mitosis and is kept in controlled inactivity until needed to maintain perfection of form and function by energizing mitosis. The immediate control of Re appears to be feedback process-dependent on the concentration of GSSG. Ultra high-frequency electromagnetic radiation of 434 MHz (UHF) will change Re from inactive to active and, in so doing, it causes resonance and/or fluorescence of the glutathione cycle which changes its radio sensitivity. Re is the primary direct target of ionizing radiation and produces the energy for mitosis. Clinical observations suggest that, in the normal cell, Re is inactive and is not killed by 3×2700 rads or 6×1650 rads yet, when active, its sensitivity value (DO) is approximately 160 rads. Using the standard radiobiological equation of response to ionizing radiation, it can be deduced that radiosensitive cancers have two or three Re units active per cell and radio resistance increases in proportion to the number of potentially active Re units per cell. Re appears to be the main cause of cancers' increased conductivity of electricity compared with normal tissue. In cancer therapy, UHF is the best radiosensitiser ever discovered (up to two or more decades). Re is also intelligent compared with non-exponential reactions but cannot be the basis of intellectual brain functions which must be based on non-electrical chemical processes.

PMID: 8577298 [PubMed—indexed for MEDLINE]

BIBLIOGRAPHY

1. Datta, J I. *American Medical Association* 271:800('94). [Microwaves with x-rays to treat malignant brain tumors.]
2. Beardsley, T. A. A War Not Won. *Scientific American* Jan. '94:130 [Lack of significant improvement in overall cancer demise rate]
3. Webb, S. & Booth A. Absorption of Microwaves by Microorganisms. *Nature* 222:1199-1200 ('69) [Frequency selective-DNA]
4. Webb, S. J. Effects of Microwaves on Normal and Tumor Cells as Seen by Laser-Raman Spectroscopy. *J. Microwave Power* 11:138 '76.
5. Grundler, W. and Keilman, F. *Physical Review Letters.* 51:1214 '83 [Strong frequency dependence on yeast prove nonthermal resonant microwave sensitivity in biology.]
6. Gandhi, o. Ed. Biological Effects and Medical Applications of Electromagnetic Energy. PP. 380-2. '90. Frequency Specific Effects.
7. Mickey, G. H. Electromagnetism and Its Effect on the Organism. *NY State J. Medicine* 63:1935-42('63) [Frequency specific killing of viruses without affecting the host; chromosomal mutation]
8. West, B. and Regelson, W. Pulsed Radio Wave Effects on Tumor Growth, *J. Microwave Power* 11:176-7('76) [Non-thermal selective]
9. Baranski, S. and Czersk, Biological Effects of Microwaves. 70-71, 132-4'76. Chromosomal Effects. Possible Genetic Effects and Influence of Microwave Radiation on Mitosis. Cellular Effects.
10. Klainer, S. and Frazer, J. Raman Spectroscopy of Molecular Species During Exposure to 100 MHz Radio-Frequency Fields. Ann NY ACAD Sci. 323-6('74) [Frequency effects on T-RNA]
11. Frohlich, H. The Biological Effects of Microwaves. Adv. Electron and Electron Physics 53:127-50('80) [Frequency specific effects on bacteria, yeast, viruses, protein metabolism, bone marrow, and Raman spectral absorption.]
12. Revzin, A. And Neumann, E. Conformation Changes in R-RNA Induced by [1 MHz] Electric Impulses. Biophys. Chem. 2:144-50('74).
13. Averbeck, D. Et al. Microwave [inter] Action in Cells With X-ray. *J. Microwave Power* 11:143 ('76)

14. Varma, M. and Raboulay. DNA Studies in Measuring Mutagenicity Caused by Non-Ionizing Radiation. *Mutation Res:*31:386-92('75)
15. Greenebaum, V. Et al. Long-Term Effects of Weak 45-75 HZ EM Fields on the Slime Mold. *Technical Report, U. Wisconsin*('75)
16. Mittler, S. Non-Thermal Radiowaves and Genetic Damage in *Drosophila*, Proc. IEEE, 6$^{th}$ Annual Meeting, Miami Beach.
17. Luczak, M. ET Al. Effect of Microwaves on Virus Multiplication in Mammalian Cells. *J. Microwave Power* 11: 173-4('76)
18. Webb, S. and Dodds, D. Inhibition of Bacterial Cell Growth by 136 GC Microwaves, *Nature* 218:374-5 ('68).
19. Glaser, Z. R. Biomedical Aspects of Radio Frequency and Microwave Radiation. *Science Policy Research Division, Lib. Congress*
20. Sevastyanova, L. and Potapov. Resonance Effect in Biological Action of Microwave Radiation. *IEEF Symposium*, ('76)
21. Schliepake, Erwin, The Medical Use of Electrical High Frequencies. English Translation of 2$^{nd}$ German Edition by R. King Brown, Actinic Press, London:'35
22. Karzmark, C. J. Advances in Linear Accelerator Design for Radiotherapy, *Medical Physics* 11:2,105-128, '84.
23. Nonthermal Effects Of Microwave Radiation On Mammalian Cells: Experimental And Theoretical Results. Stephen F. Cleary, Ph.D., Bioelectromagnetic Laboratory, Department of Physiology and Biophysics, Medical College of Virginia, Virginia Commonwealth University, Richmond, Va. 23298.

The precise degree of experimental control afforded by in vitro exposure systems has permitted investigation of direct cell physiological responses to microwave radiation under nonthermal exposure conditions. A variety of cellular alterations have been attributed to nonthermal microwave interactions. Such effects include: 1) altered cation transport and binding; 2) ion channel kinetic changes; 3) biochemical alterations; 4) effects on the mitotic cycle; and 5) modulation of cell proliferation and transformation. Whereas such effects are generally consistent with microwave-induced alteration of signal transductive pathways at the membrane surface detailed mechanistic has been elusive. Recent theoretical studies indicate spatially nonuniform microwave energy absorption on cell membrane surfaces due to field coupling with cell membrane bound water molecules. Predictions based on this interaction model will be described together with supporting experimental data derived from studies of microwave and radiofrequency radiation effects on cytokine/receptor binding.

SUMMARY OF THE INVENTION

The present invention discloses a number of new uses for the method of Cyrulnik, which can be summarized into the following categories:

MEDICAL DLAGNOSTIC CAPABILITIES—at low energy levels, the method of Cyrulnik may be extended to be used as a sophisticated medical diagnosis tool. The present invention discloses uses focused on localizing and imaging a variety of biological and chemical systems and conditions for further characterization rather than for destruction;

TREATMENT OF SPECIFIC PATHOLOGICAL CONDITIONS—several new therapeutic uses have developed with advances in medical knowledge. The present application discloses, for example, new methods of use directed treatment of infectious diseases, treatment of general medical diseases such as atherosclerosis and autoimmune diseases, storage diseases, and genetic therapy;

NON-INVASIVE SURGERY—provides a truly non-invasive method of eliminating unwanted tissue anywhere in the body, effectively allowing non-invasive surgery;

REGENERATION OF CELLS AND TISSUES—Selective destruction/activation of specific cells allows for regeneration of cells and tissues, such as spinal cord regeneration.

DESCRIPTION OF THE PREFERRED EMBODIMENTS

Figure 1:
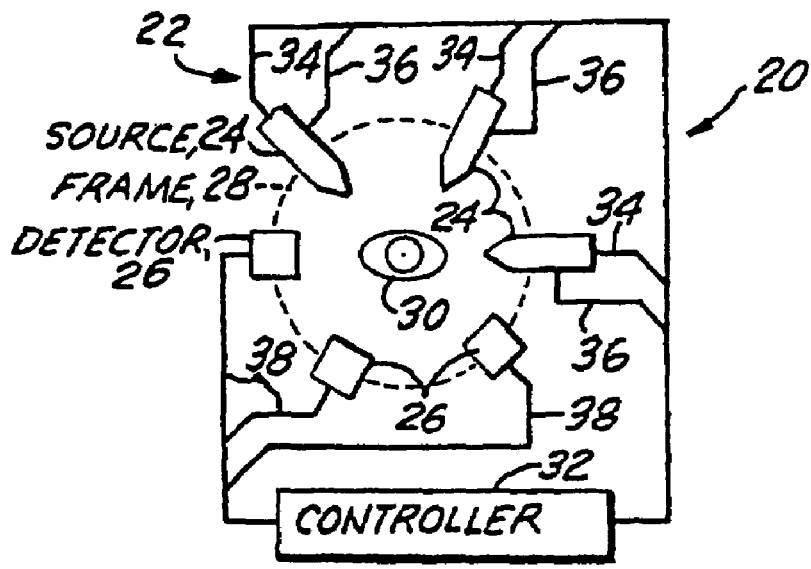
FIG. 1 illustrates a prior art diagrammatic view of a CT scanner modified for microwave modulation.
Figure 2:
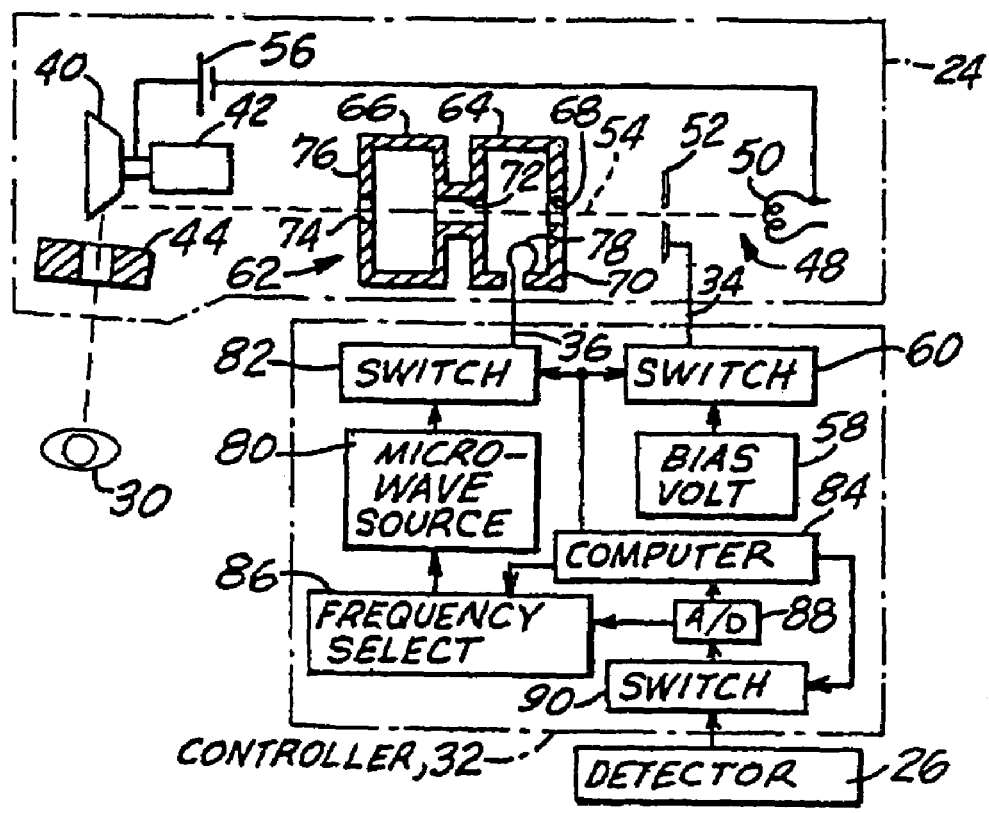
FIG. 2 illustrates a prior art system for microwave modulation.
Figure 3:
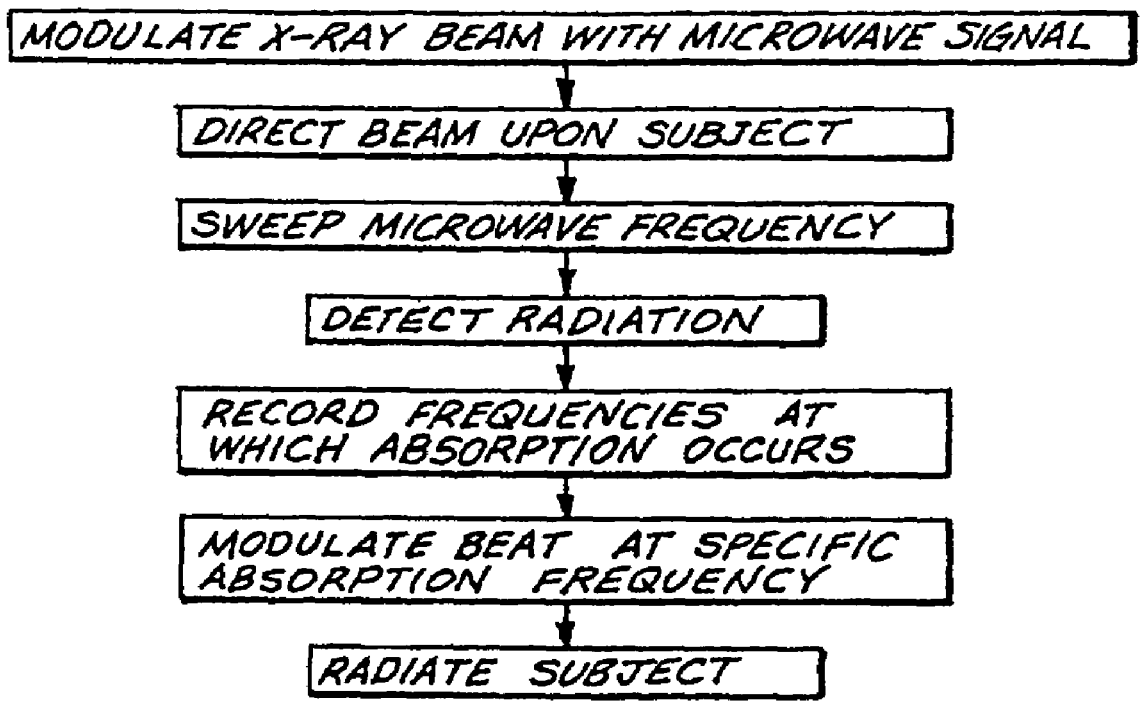
FIG. 3 illustrates a prior art process for radiotherapy using the device of FIG. 2.

While this invention is illustrated and described in a preferred embodiment, the device may be produced in many different configurations, forms and materials. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

Throughout the specification and claims, the preferred frequencies used are generally cited in the microwave range, however, other frequency ranges may be used without departing from the scope of the present invention. For example, viral matter may respond better to RF frequencies. In addition, the examples cite the invention practiced using a CT device on a patient, however, other configurations providing the modulated x-ray input may be practiced and samples may be used as a source of cell or tissues without departing from the scope of the present invention. Thus, the invention is equivalently applied to blood, tissue, and/or micro arrays (e.g., DNA, protein, etc.).

The present invention is used in various embodiments to locate, diagnose and treat many specified cells and tissues, so as to provide the capability for effectively imaging, performing noninvasive surgery, and treatment of a wide variety of medical diseases and ailments.

The approach is empirical, in that treatment can be performed even on conditions whose precise cause is still being determined, such as atherosclerotic narrowing of coronary and cerebral arteries.

The present invention is practiced on a MM Scanner™ (a modified CT scanner whose ordinary x-ray beam is modulated in the microwave frequency range by a device known as a klystron). The use of an electron beam fast CT Scanner represents a preferred implementation of the device, although other functional equivalents and future equivalents may be used without departing from the scope of the present invention. The system has the non-linear effect of imposing a component of microwave or RF frequency in the radiation by turning the beam of electrons generating the x-rays on and off at frequencies which are calculated to be selectively absorbed by large (macro) molecules such as the DNA and their RNA transcripts which make up the genes responsible for cell growth. Since each such type of molecule has its own unique signature of electrons orbiting it, an abnormal gene or similar substance, is expected to absorb the modulated beam selectively at some particular frequency of modulation, with negligible absorption by normal molecules, much as a signal on a TV carrier wave is picked up by a circuit tuned to one particular channel. This arrangement allows for delivery of radiation to the abnormal entity, with no significant harm to normal tissue. The present invention can also be effective for entities that cannot be imaged as a solid mass, such as viral particles and leukemic cell DNA. One embodiment being the use of micro arrays of DNA/RNA or proteins, and another being comparing patient's blood cell absorption after relapse, if any, to previous absorption profile. This might also apply to getting a library of known frequencies of absorption by specific pathological entities, such as the abnormal storage material in Parkinson's disease and probably Alzheimer's disease, by comparing absorption profiles in such patient's with those of normal control subjects.

Figure 5:
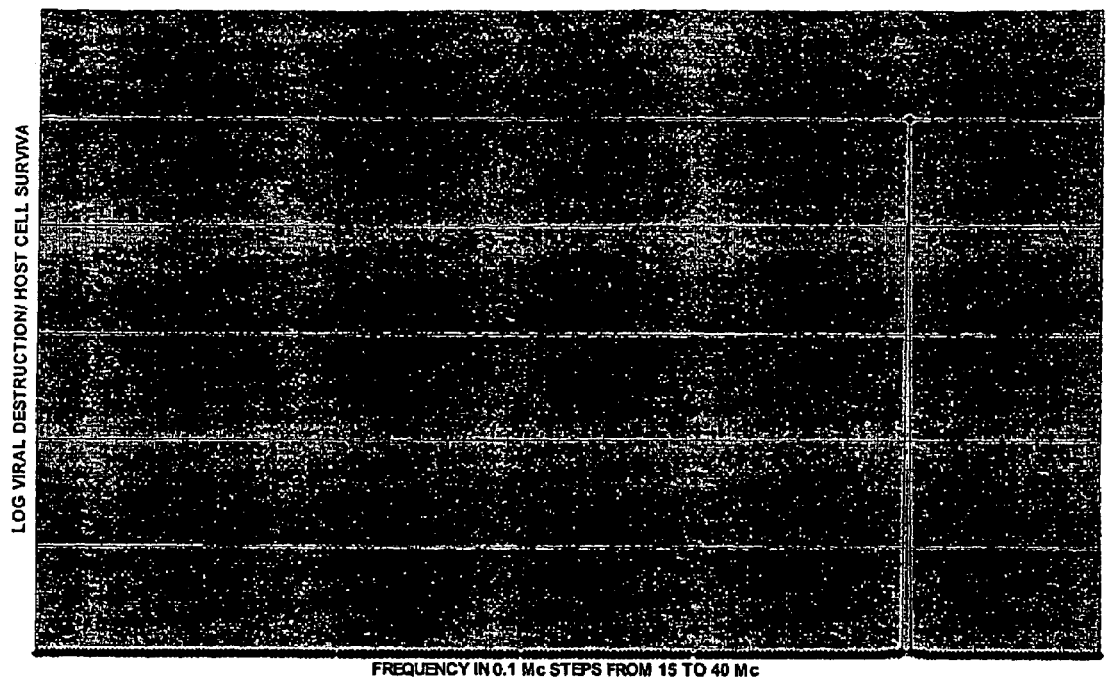
FIG. 5 illustrates frequency-specific absorption and destruction of phage virus by RF MW, and FIGS. 6a-6d, collectively, illustrate a method for rapid reconstruction of the CT image, by selecting the scan that is generated specifically at the frequency uniquely absorbed by a pathological entity (such as a tumor) and not at other frequencies of modulation.

FIG. 5 illustrates frequency selective destruction of virus (phage) inhabiting living cells (*E. Coli*) without harming the host cell. The frequency was swept from 15 to 40 Megacycles per second in steps of 0.1 Mc./sec. At 35.5 Mc./sec. There is strong destruction of the virus and, conversely, marked survival of the host cells.

The great advantage of this method over conventional radiotherapy results from its selectivity: whereas standard radiotherapy is markedly limited by the concomitant destruction of normal tissue, (as is also the case for virtually all known forms of chemotherapy), there is little concern for such side: effects with the MM scanner™, resulting in both tremendously enhanced safety and effectiveness, and the promise of a cure.

CT Scanning is used in this technique for a number of reasons:
(1) It localizes the site of origin of the entity absorbing the modulated beam, allowing direct imaging thereof, revealing its nature and location
(2) An abnormality can be visualized entirely in isolation from any other tissue, confirming its selective absorption
(3) Since CT divides the x-ray beam into many small parts, a minute dose of radiation can be administered safely in this initial detection process which nevertheless, because of its selective absorption, permits imaging of the absorbing tissue
(4) Since multiple scans at different microwave frequencies of modulation are imaged, a rapid scanner is advantageous, and has the additional virtue of eliminating the problem of over-heating the target in the x-ray tube with current tube design, and
(5) Empirical Determination of the absorptive curative frequency is extremely rapid compared to biochemical and immunological paradigms to find selective effects.

Initially, a minute dosage of microwave modulation is applied to the CT scan beam, calculated to be sufficient to image the target tissue without harming normal tissue. An empirical iterative series of such images zeroes in on the frequency of selective absorption.

Adjusting the parameters and paradigm of modulation, such as decreasing the amplitude of modulation in square wave fashion without completely turning off the electron beam, can be used to provide continuous x-ray energy in addition to the modulated form, for enhancing demodulation and focusing. A similar virtually continuous x-ray beam, which is nevertheless modulated, can be formed by using two klystrons such that one turns the electron beam on while the other turns it off, and vice-versa, with arbitrary interval between them. Focusing can also be enhanced with focusing coils, which may correct defocusing.

If a rapid CT scanner is used, the frequency of the modulating microwave can be swept through arbitrarily small bands in stepwise fashion at each target, allowing retrieval of a complete scan at each frequency band by interrogating the detectors for absorption at, and only at, the precise delay after the start of modulation which that given frequency band was incident. (In a typical scan with total time of 100 milliseconds, each of the thousand targets of an ebt scanner has a nominal dwell time of 100 microseconds, allowing 3 cycles of $(10^5)$ frequency bands of 3 gigacycle waves $[(10^{-9})(10^5)=(10^{-4})$ seconds] to be sequenced. Therefore, at 1 gigacycle, 30,000 candidate frequency bands could each be used to create a scan, which as shown in the original patent, would suffice for imaging because of greatly enhanced absorption at the resonant frequency). This would allow interrogation for absorption of the transcribed DNA of the entire human genome.

Figure 4:
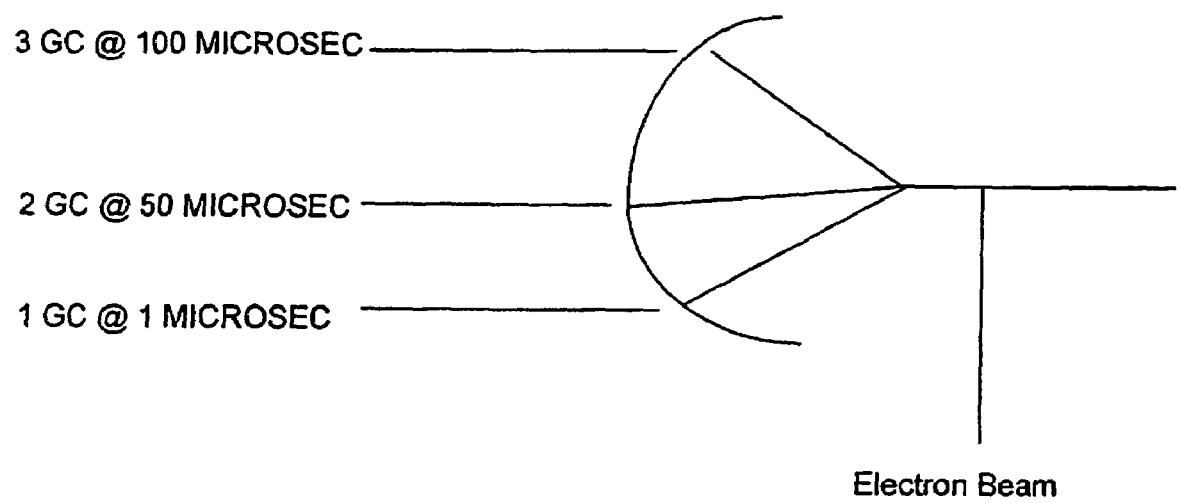
FIG. 4 illustrates sequential frequency modulation at each target for time-locked retrieval.

FIG. 4 shows a method of sweeping the microwave frequency modulating the electron beam generating the x-rays at each target of an array of identical x-ray targets. The modulating frequency is varied sequentially in selected steps over the desired range, illustrated here as from 1 to 3 gigacycles per second. A scan can be generated by specifying the time delay from onset of modulation to the time that a specified frequency was operant, and using that time delay at each detector to construct a CT scan resulting from modulation at that frequency only.

To facilitate reconstruction of the scans for reasonable throughput, the software need only compare one or a small number of pixels inside the known area of interest (e.g., tumor) with a similar number outside, since a complete scan is only needed at the frequency where there is absorption in the tumor but not outside, which would be not more than about 1-10 frequencies, corresponding to the abnormal genes in the tumor. Therefore, the time to reconstruct two single scans in the unmodulated mode with $(512^2)=36,000$ pixels would be the same as comparing the above-mentioned pixels, two for each frequency, for the 30,000 frequencies tested. Throughput would thus be on the order of taking 1 diagnostic rapid scan, 2 for each allele plus one for mutation, and one therapeutic irradiation at full duty cycle (at least 8 reconstructs and 6 comparisons), for a total of about 2 minutes.

Diagnostic Capabilities

CT scanning, used in some embodiments, can provide diagnostic information equivalent or superior to state-of-the-art MRI spectroscopy. Thus: (a) target macromolecules are imaged without confounding artifact, and their nature can be determined directly by comparison with known frequencies of absorption of the various known macromolecules without use of injected dyes, (b) entire systems of cell types are visualized in extended is distribution, such as functional distributed groups of neurons producing or having receptors for various neurotransmitters or the distribution of cells carrying a certain antigen or receptor, and (c) specific normal and abnormal cells and materials are detected and can be isolated. Therefore, detection of the presence of an abnormal gene, for example, in an individual becomes relatively simple and definitive, as a rapid alternative to more intricate methods of genetic screening in current use, and (d) the detection of diseases such as Alzheimer plaques and tangles, or herpes simplex virus are only a few examples of the diagnostic power of this technique in obtaining information that would replace invasive procedures such as brain biopsy or PCR amplification of spinal fluid, currently needed for definitive diagnosis of these conditions having no definite biological marker on laboratory testing.

Figure 6A:
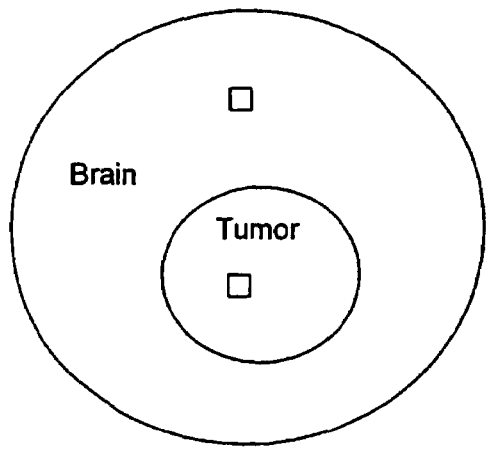
Figure 6B:
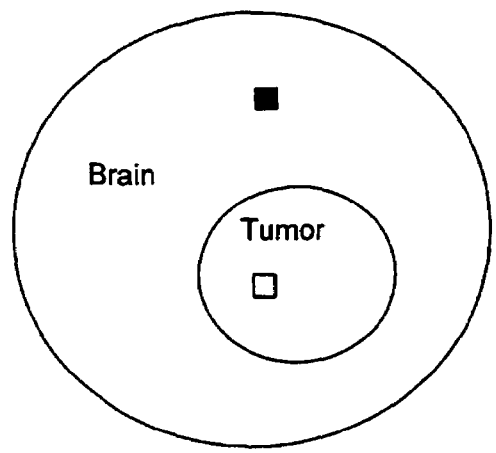
Figure 6C:
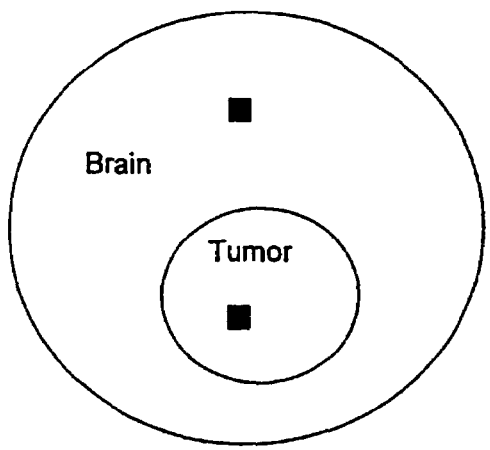
Figure 6D:
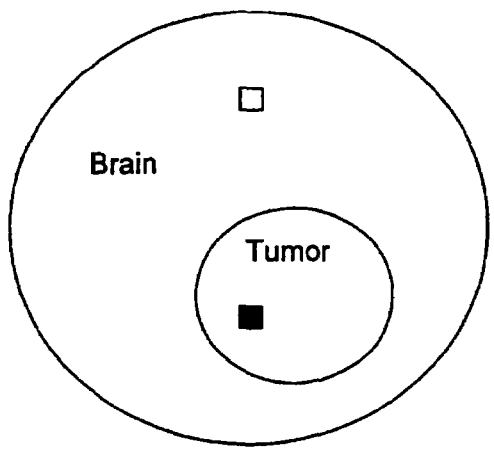

FIGS. 6a-6d, collectively, illustrate a method for selectively reconstructing only the image which shows the pathological entity alone that absorbs the modulated x-rays uniquely at one of several frequencies of modulation. FIGS. 6a-6c illustrate scenarios for frequencies that do not provide absorption by a pathological entity only. FIG. 6a shows non-absorption (white pixels) in both tumor and brain tissues; 6b shows absorption (black pixel) by the brain, but not the tumor (white pixel); 6c shows absorption by both brain and tumor (both black pixels). FIG. 6d illustrates the correct frequency of modulation and corresponding desired imaging, aborption by the tumor (black pixel), but not the healthy brain tissue (white pixel). This method: (a) confirms that there is absorption of the modulated x-rays by the pathological entity and not by normal structures; (b) identifies the frequency of modulation that is absorbed only by the pathological entity, as is determined by ascertaining the time delay from the beginning of modulation, as noted in FIG. 4, at which this imaged scan was generated; (c) makes throughput time reasonably short by not reconstructing images in which there is absorption by normal structures, and/or not by the pathological entity.

Specific diagnosing applications include, but are not limited to:

Transmissible spongiform encephalopathy (mad cow disease)—currently, to detect this disease in animals, which can be transmitted to humans by ingesting their meat, examination of their brains is required, resulting in the loss of significant numbers of normal cattle since the prolonged incubation period of the responsible abnormal prior protein precludes early clinical detection. Selective absorption of radiation by the abnormal prion would allow imaging with this device as a non-invasive biological marker with tremendous public health benefits as well as great savings to the cattle industry.

Security screening—current methods of screening baggage and passengers boarding commercial vehicles or entering large gatherings of people rely on metal detection or on x-ray imaging of baggage using the shape of visualized objects for identification. A much more accurate identification could be made by the MM scanner since the nature or composition of the scanned object would be identified. For example, since each substance is made of unique molecules, a container filled with explosives would light up at a frequency of modulation that a container of the same shape containing a harmless substance would not. Similarly, an envelope containing anthrax bacilli would be easily differentiated from other mail.

Selectively destroying pathogens in media entering other "clean" environments, including blood and blood products for transfusion Military applications:

Biological Warfare—while counter-measures to some diseases that could cause mass casualties exist, they are able to be circumvented by genetic engineering. For example, it is known that the Soviet Union produced strains of germs that are engineered genetically to be resistant to current therapies, be they antibiotics or vaccines. Since the MM scanner detects the frequency that a particular agent absorbs as it exists at the time of use, genetic engineering would pose no obstacle to being able to eradicate the new strain.

Microwave modulation of x-rays permits irradiation to selectively absorbing targets that is orders of magnitude greater than conventional radiation, yet need not be focused, since there is relatively negligible absorption of other objects and materials in the same field. Thus, selected entities with known imaging characteristics could be destroyed without harming-people for example. This could be applied with minute screening doses at checkpoints with high suspicion of terrorists (with little harm to people) to detect concealed explosives.

Treatment of Specific Pathological Conditions

Other applications include, but are not limited to, treatment of other pathological conditions involving large molecules, such as:

Atherosclerotic occlusion of arteries causing heart attack and stroke, can be treated noninvasively by this technique at the time of initial imaging of the acute episode since the clot consists of a macromolecular conglomeration that can be non-invasively destroyed by selective absorption of the microwave modulated radiation Experimental evidence already supports frequency selective destruction of viruses and bacteria in this region of the spectrum, although a system for in vivo delivery of the radiation was not available hitherto as is now the case with the MM Scanner™

AIDS and other viral diseases including but not limited to Ebola, Smallpox, SARS, hepatitis, encephalitis, meningitis, and influenza and endocarditis.

Autoimmune diseases including, but not limited to, rheumatoid arthritis, diabetes, collagen vascular diseases, Guillain-Barre's disease, chronic inflammatory neuropathies, Crohn's disease, ulcerative colitis, asthma, allergic rhinitis, glomerulonephritis, organ transplant rejection, graft versus host disease, allergic encephalomyelitis, post-viral encephalitis, and thyroiditis. A number of diseases in which the body reacts against its own tissue have resisted cure and remain chronic, such as arthritis, and, as recently noted, diabetes. While immunosuppressive drugs exist, they are generally toxic because they are nonspecific, altering the entire immune system. The MM Scanner™, however, would have a selective effect on the macromolecular complexes involved or on their genetic precursors and cells of origin, offering the possibility of prevention or cure. Since the target need not be in a single physical locus, disease progression itself may be halted as well as elimination of offending autoantibodies in active lesions. (Monoclonal antibodies have limited effectiveness in these cases because they are either destroyed as foreign to the patient's immune system or too humanized to recognize human antibodies as foreign.

Malaria, which is, on a world-wide basis, the greatest killer.

Tuberculosis and other Mycobacterial infections

Leprosy, which require years or lifelong treatment with medication

Fungal infections whose systemic treatment carries a significant risk of serious side effects Bacterial Diseases which are resistant to drugs as well as those whose rapid detection would be extremely important, such as anthrax Post-Viral diseases, for which, in general, there are no available medications, such as acute disseminated encephalomyelitis, Dawson's post-measles and post-influenza encephalitis Genetically engineered resistant organisms, such as smallpox virus, known to have been designed to resist current immunization, and anthrax rendered resistant to antibiotics Prion diseases including but not limited to Jacob-Creutzfeld disease in humans and spongiform encephalopathy in animals Chronic or disseminated infectious diseases such as Lyme disease, syphilis and other spirochetal diseases, and ricketsial diseases.

Atherosclerosis, which narrows the arterial supply to vital structures such as the brain and heart, is the number one killer in the U.S. Despite the myriad of research on this condition, there is no known cure. Current management is quite invasive, consisting of open heart bypass grafting, or a number of less invasive procedures on these vital organs, such as angioplasty of various types. These atherosclerotic plaques are distinctive structures containing specific types of cells and large molecular collections such as phospholipids and cholesterol. As such, they would be expected to absorb microwave modulated radiation selectively. This can be easily determined by CT visualization in the MM Scanner™, which would indicate the ability to eliminate the plaque or its progression. Moreover, this could be done noninvasively both for focal narrowing as well as diffuse disease, including sites inaccessible to invasive techniques such as surgery and angioplasty The ability of the MM Scanner™ to target selectively an abnormal gene offers the exciting possibility of being able to modify the transmission of inherited diseases: by eliminating those germ cells carrying the abnormal gene, it would be possible to render the affected parent-free of any germ (reproductive) cells carrying the abnormality. To minimize ethical concerns and to offer a single therapeutic session, this would best be done prior to conception. Even if the gene is dominant, a parent carrying it has a 50% chance of having normal offspring, but currently there is no other way known to eliminate the other 50% possibility of an affected child, short of either sterilization or abortion, and that after intricate and invasive genetic testing procedures on the fetus.

To eliminate the gene in individuals already affected by an inherited disease, such as Huntington's Chorea (in which initially normal appearing people develop severe mental deterioration and uncontrollable movements in middle life), one would have to target all of their cells, or at least those in the affected organ (the brain in this case). Since only certain systems of neurons appear to be affected, it is possible that the abnormal gene is only activated in certain cells, offering the possibility that selective irradiation of these abnormal genetic transcripts by the MM Scanner™ may halt or cure the disease.

In various diseases such as Alzheimer's, Parkinson's, Jacob Creutzfeld & other storage diseases, an abnormal material accumulates in the tissues which correlate with the pathological manifestations of the disease. Whether this is due to an abnormal gene product or lack thereof, as in the case of hereditary forms of these diseases, or a sporadic defect that results in an abnormally truncated peptide or protein that then forms macromolecular aggregates, or to a pathological isoform that then induces formation of a cascade of macromolecular sheets of the abnormal isoform as in prion diseases, diagnosis and treatment of these conditions can be accomplished by detecting the pathological material using microwave modulated x-rays at characteristic frequencies, with CT scanning using microwave modulated x-rays to detect characteristic distributions of the pathological material, for diagnosis, and irradiating at increased duty cycle to destroy the pathological material. This would halt the progression of these diseases and may reverse the death of those cells not yet irreversibly damaged.

The destruction of pathogens with the MM Scanner™ is one of the likeliest applications for several reasons:

These microbes are foreign organisms with great probability of significant difference in frequency of absorption than human nucleic acid. Obviously, where antimicrobial medication is available or the disease is self-limited (such as the common cold), this application would be limited.

Non-Invasive Surgery

The present invention use of the MM Scanner™ provides a truly non-invasive method of eliminating unwanted tissue anywhere in the body, effectively allowing non-invasive surgery.

Specific non-invasive surgery applications include, but are not limited to:

Bile acids around which gallstones develop may form large enough conglomerates of molecules to respond to the range of frequencies in the microwave range, allowing the possibility of their dissolution by the MM ScannerTM, and eliminating the need for another very common operation (cholecystectomy).

One of the most common operations in neurosurgery and in orthopedics consists of removal of a herniated intervertebral disc. Non-invasive alternatives to this procedure have been desperately sought, as is attested to by the popularity of the attempt to treat this condition with chymopapin injections into the disc (itself invasive and dangerous because of allergic reactions to the injected enzyme), and the literature is replete with cases of failed back operations. Since the disc material consists of a gel-like conglomerate of large macromolecules, the MM Scanner™ has the potential to destroy selectively the offending disc material in a totally non-invasive fashion.

Surgery is often done to remove tissue that is otherwise normal but which is pathologically excessive, such as in the case of nerve entrapment syndromes, where fibrous tissue builds up as a result of repetitive trauma (often occupational) and compresses an adjacent nerve. Localized irradiation of this tissue with the MM Scanner™ could reverse this process by stopping the continued overgrowth of these connective tissue cells Hearing loss due to otosclerosis, the most common cause of heredity deafness, is due to overgrowth of bone in the middle ear. Stopping this process with the MM Scanner™, by selectively de-immortalizing the growing bone cells in this region could be another widespread application of this technology.

Not all abnormal cells that should be eliminated are growing, but their pathological nature is likely to be reflected in their macromolecular makeup, whether genetically inherited or due to direct damage that is passed on to daughter cells as a somatic mutation, or present as an injury in common to a group of cells (e.g., affecting their macromolecular membranes). For example, foci of abnormal cells producing epilepsy are now able to be removed surgically after being imaged by PET scan. If the abnormal focus is imaged by the MM Scanner™ it could be eliminated non-invasively without surgery Whereas surgery is not applicable to generalized epilepsy, selective absorption of modulated radiation would, in fact, apply to a diffuse system of cells, such as those involved in non-focal epilepsy, as well as in dyskinesias, ectopic tissue such as glandular tissue (e.g. excess thyroid) and endometriosis, sarcoid and xanthomata, to name a few, allowing noninvasive cure Disenabling of a functioning system is also sometimes performed surgically, such as lesioning the spinal pain tracts in cases of intractable pain. This could be accomplished non-invasively by selective destruction of systems of sensory cells that can be imaged using the MM Scanner™

Regeneration of Cells and Tissues

Other applications include, but are not limited to, regeneration of cells and tissues.

It is now known that it injured spinal cord does not regenerate because certain cells secrete substances in the lesion preventing regrowth. Selective destruction of these cells or the DNA/RNA transcripts of the genes that produce these inhibitory molecules should allow for regeneration. The myelinated tracts of the spinal cord, unlike peripheral nerves, do not regenerate despite intact cell bodies proximal to the lesion and, in many cases, anatomical continuity of the scaffolding connecting these to the lower motor or sensory neurons more distally. Recent studies have determined that this is due to the presence of inhibitory molecules on the myelin sheaths surrounding the nerve fibers that otherwise could grow back. The modulated microwave x-rays have the potential to non-invasively destroy these molecules either as they exist in the macromolecular myelin sheath or at the stage of DNA transcription in the oligodendrocytes that produce them. In the case of totally transected cord requiring insertion of scaffolding, such as with stem cells, a preliminary step is still required in which the inhibiting myelin or its contained macromolecules is destroyed, a step that could still be done as described non-invasively with minimal damage to non-inhibitory tissue The cloning of an entire organism with its component tissues from a the set of genes of a somatic differentiated cell, as well as the production of differentiated cells from stem cells, which have already been accomplished, indicates that the genetic machinery, the genome, which is the same in the nuclei of all cells of an individual, contains the entire program for sequentially reproducing the processes of differentiation.

To start the process, or to enter the program at any point, it is simply needed to supply the proper environment to turn on that set of genes by re-creating the external conditions that exist when the cell is at that stage of differentiation: for a whole organism, one inserts the somatic nuclear DNA into an enucleated egg cell; for producing T cell receptors, the stem cell is incubated with white blood cells. This capability of the environment surrounding the DNA to turn it on at any desired point, after which it will go through the entire subsequent sequence of steps in the program of differentiation, implies that there are transcription factors available to the DNA to carry out that series of steps, provided that an initial reaction occurs of a chemical nature, such as the binding to the DNA of the transcription factor that starts the program at that particular step. The nature of the process that triggers such binding, without which differentiation does not occur despite the availability of the transcription factors to the DNA, currently is empirical and not well understood.

When two molecules bind together, they enter into a combined state whose energy level is lower than before the reaction. To make this happen, it is often necessary to supply energy, such as heat, which raises the energy level of the molecules from which they can subsequently fall when they combine; without the temporarily added energy, the molecules remain separate entities even if in close proximity. Since heat will supply energy in a non-specific way to all the reactants present, many molecular species will bind to each other when heat is supplied, precluding a precise triggering reaction to start the program of differentiation. When electromagnetic energy is absorbed, however, no free energy is produced as a byproduct, allowing precise delivery of exactly the amount of energy needed to change the configuration of the reacting species to the new combination product. In other words, the delivery of electromagnetic energy that is selectively absorbed by potentially binding molecules will trigger their reacting with each other. In the case of macromolecules such as DNA, the frequencies absorbed are in the microwave range. The precise amount of energy needed the trigger the program to start by binding a transcription factor to the DNA can be delivered by controlling the frequency of the microwaves, since the energy of electromagnetic waves is locked to their frequency. By empirically determining which frequencies are being absorbed by cells that are the step-wise process of differentiation, a means of driving the initial reaction that starts the growth and differentiation program can be realized. By detecting such frequencies in vivo and supply them to a particular tissue, regeneration will proceed.

CONCLUSION

A system and method has been shown in the above embodiments for the effective implementation of a system and method for diagnosing and interacting with selected specific entities containing or comprised of macromolecules. While various preferred embodiments have been shown and described, it will be understood that there is no intent to limit the invention by such disclosure, but rather, it is intended to cover all modifications and alternate constructions falling within the spirit and scope of the invention, as defined in the appended claims. In fact, this technique should work no matter how target molecules differ from normal cells, and does not depend on oncogenes per se: it simply detects at which frequency the entity containing or comprised of the target molecules, but not non-target molecules, absorb the radiation, whether due to oncogenes, greater amounts of macromolecules, higher levels of protein synthesis or metabolism, or morphological, physical or chemical differences. The specific frequency range should not be limited to microwaves, but include any frequency range which interacts with a target medium as per the present application.

The invention claimed is:

1. A method for medical diagnosis of a patient by detecting a target macromolecular structure, which comprises:
   (a) generating a low level diagnostic x-ray beam;
   (b) providing an amplitude modulation of the x-ray beam with an amplitude modulating signal at a predetermined or empirically determined microwave frequency or range of sequential microwave frequencies;
   (c) directing the x-ray beam upon the patient;
   (d) detecting and imaging one or more target macromolecule structures involved in production of diseases which absorb said amplitude modulated x-ray beam at said predetermined or empirically determined microwave frequency or range of sequential frequencies; and (e) comparing the microwave frequency or range of sequential frequencies with known frequencies of absorption of known macromolecules.

2. The method of medical diagnosis of claim 1, wherein a microwave modulating device provides said amplitude modulation, thereby modulating a CT scanner by said amplitude modulation.

3. The method of medical diagnosis of claim 1, wherein said one or more target macromolecule structures comprise or contain one or more cells selected from the group consisting of: oncogenes, abnormal genes, Alzheimer plaques, Alzheimer tangles, pathogens, biological markers, genetic precursors, cells of origin, germ cells, malignant cells, antibodies, atherosclerotic plaques, macromolecular conglomerates, and macromolecular storage disease aggregates.

4. The method of medical diagnosis of claim 3, wherein said pathogen is a virus selected from the group consisting of: herpes simplex virus, AIDS virus, Ebola, smallpox, SARS, hepatitis, encephalitis, spongiform encephalopathy, meningitis, influenza, oncogenic viruses, endocarditis/myocarditis, virus, herpes zoster, polio virus, measles virus, mumps virus, rubella virus, corona viruses, and arthropod borne viruses.

5. The method of medical diagnosis of claim 1, said method further comprising:

determining said predetermined or empirically determined microwave frequency or range of sequential frequencies as in step (b) by a process selected from the group consisting of: absorbing by irradiating DNA, RNA or protein microarrays; using computed tomography to image the absorbing entity containing or comprising said macromolecular structure; and varying the frequency of modulation to determine those frequencies that are uniquely absorbed by the target macromolecular structure or entity containing or comprising the target macromolecular structure.

6. A method for security screening by detecting a target macromolecular structure, which comprises:

(a) generating a low level diagnostic x-ray beam;

(b) providing an amplitude modulation of the x-ray beam at a predetermined or empirically determined microwave frequency or range of sequential microwave frequencies;

(c) directing the x-ray beam upon an object or subject;

(d) detecting and imaging one or more target macromolecular structures which absorb said amplitude modulated x-ray beam at said predetermined or empirically determined microwave frequency or range of sequential frequencies;

(e) comparing the microwave frequency or range of sequential frequencies with known frequencies of absorption of known macromolecules; and (f) identifying said target macromolecular structure.

7. The method of security screening as in claim 6, further comprising:

(g) destroying said target macromolecular structure by applying a high level modulated x-ray beam at said predetermined or empirically determined microwave frequency or range of sequential frequencies.

8. The method of security screening as in claim 6, wherein the object or subject is selected from the group consisting of: persons, vehicles, packages, blood, blood products, and travel baggage.

9. The method of security screening as in claim 6, wherein the or more target macromolecular structures are selected from the group consisting of: explosives, contraband, chemical weapons, biological weapons, viruses, prions, bacteria, fungi, pathogens in media, pathogens in blood, and pathogens in blood products for transfusion.

10. A method of treatment of a pathological condition by destroying a macromolecular structure, their genetic precursors and cells of origin which comprises:

(a) generating a low level diagnostic x-ray beam;

(b) providing an amplitude modulation of the x-ray beam with an amplitude modulating signal on a CT source at a predetermined or empirically determined microwave frequency or range of sequential microwave frequencies;

(c) directing the x-ray beam upon a patient;

(d) detecting and imaging one or more target macromolecule structures involved in production of diseases which absorb said amplitude modulated x-ray beam at said predetermined or empirically determined microwave frequency or range of sequential frequencies;

(e) comparing the microwave frequency or range of sequential frequencies with known frequencies of absorption of known macromolecules;

(f) recognizing a pathological condition as comprising one or more target macromolecular structures; and (g) applying said modulated CT source to said target macromolecule structures to destroy said pathological condition.

11. The method for treating a pathological condition as in claim 10, wherein the pathological condition is selected from the group consisting of general medical diseases, malignancies, infectious diseases, prion diseases, storage diseases, immune diseases, autoimmune diseases, degenerative diseases, and genetic diseases.

12. The method for treating a pathological condition as in claim 11, wherein the pathological condition is an autoimmune disease and wherein said method identifies and destroys the autoimmune disease carrying macromolecular complexes.

13. The method of treating a pathological condition as in claim 12, wherein the autoimmune disease is a diseases where the body reacts against its own tissues.

14. The method of treating a pathological condition as in claim 12, wherein said autoimmune disease is are selected from the group consisting of rheumatoid arthritis, diabetes, collagen vascular diseases, Guillain-Barre's disease, chronic inflammatory neuropathies, Crohn's disease, ulcerative colitis, asthma, allergic rhinitis, glomerulonephritis, allergic encephalomyelitis, post-viral encephalitis, Dawson's encephalitis, psoriasis, organ transplant rejection, graft-versus host disease, and thyroiditis.

15. The method for treating a pathological condition as in claim 10, wherein the pathological condition is selected from the group consisting of: thrombrotic or atherosclerotic occlusion or narrowing of arteries causing heart attack and stroke, selective destruction of viruses, AIDS, immune diseases, malaria, mycobacterial infections, fungal infections, rickettsial diseases, spirochete infection, genetically engineered resistant organisms, drug resistant pathogens, arthritis, inherited diseases, Huntington's Chorea, Alzheimer's disease, Parkinson's disease, prion diseases, Jacob Creutzfeld disease, storage diseases characterized by accumulation of abnormal or excessive material in body cells or tissue, Ebola, smallpox, SARS, hepatitis, encephalitis, meningitis, influenza, parasitic diseases, endocarditis/myocarditis, herpes zoster, polio virus, measles virus, mumps virus, or rubella virus, autoimmune diseases, diabetes, collagen vascular diseases, Guillain-Barre's disease, chronic inflammatory neuropathies, Crohn's disease, ulcerative colitis, asthma, allergic rhinitis, leprosy, glomerulonephritis, allergic disseminated encephalomyelitis, post-viral encephalitis, Dawson's encephalitis, psoriasis, organ transplant rejection, graft-versus host disease, thyroiditis, malignancies, abnormal genes, and germ cells carrying abnormal genes.

16. A method for performing non-invasive surgery using imaging or detection of a target macromolecular structure, said method comprising:
    (a) generating a low level diagnostic x-ray beam;
    (b) providing an amplitude modulation of the x-ray beam with an amplitude modulated signal from a CT source at a predetermined or empirically determined microwave frequency or range of sequential microwave frequencies;
    (c) directing the x-ray beam upon a target object of a patient;
    (d) detecting and imaging one or more target macromolecule structures which absorb said amplitude modulated x-ray beam at said predetermined or empirically determined microwave frequency or range of sequential frequencies;
    (e) comparing the microwave frequency or range of sequential frequencies with known frequencies of absorption of known macromolecules;
    (f) recognizing one or more target macromolecular structures; and
    (g) applying said modulated CT source to said target macromolecule structures to modify or destroy said target macromolecular structures.

17. The method of claim 16, where said target object is selected from the group consisting of: spinal herniated disc material, bile acids around which gallstones develop, gallstones, normal but pathologically excessive tissue, nerve entrapment syndromes, middle ear osteoblast bone overgrowth, abnormal cells producing epilepsy, diffuse systems of cells of ectopic tissue, malignant cells, glandular tissue, endometriosis, sarcoid, xanthomata, cells responsible for dyskinesias, spinal pain tracts in cases of intractable pain, and one or more target macromolecule structures which control cellular receptors.

18. The method of claim 17, where the one or more macromolucular structures which control cellular receptors are selected from the group consisting of: hypersensitive or increased numbers of cellular receptors, said control consisting of elimination of a target object comprising one or more target macromolecule structures.

19. A method for regeneration of cells and tissues using imaging or detection of a target macromolecular structure, said method comprising:
    (a) generating a low level diagnostic x-ray beam;
    (b) providing an amplitude modulation of the x-ray beam with an amplitude modulated signal from a CT source at a predetermined or empirically determined microwave frequency or range of sequential microwave frequencies;
    (c) directing the x-ray beam upon a patient;
    (d) detecting and imaging one or more target macromolecule structures involved in production of diseases which absorb said amplitude modulated x-ray beam at said predetermined or empirically determined microwave frequency or range of sequential frequencies; and
    (e) comparing the microwave frequency or range of sequential frequencies with known frequencies of absorption of known macromolecules; and
    (f) applying said modulated CT source to said target macromolecule structures to regenerate cells and tissues.

20. The method for regeneration of cells and tissues of claim 19, where said regenerated cells and tissue comprise the spinal cord.

21. The method for regeneration of cells and tissues of claim 20, wherein said spinal cord is regenerated by non-invasively destroying specific target macromolocules as they exist in the macromolecular myelin sheath or at the stage of DNA transcription in the oligodendrocytes that produce them.

22. The method for regeneration of cells and tissues of claim 20, wherein said spinal cord is a totally transected cord, and wherein immediately prior to step (f) above, inhibiting myelin or its contained macromolecules is performed by selection of said myelin or contained macromolecules as target macromolecule structures.

23. The method for regeneration of cells and tissues of claim 19 comprising a process selected from the group consisting of: cloning an entire organism with its component tissues from a set of genes of a somatic differentiated cell, producing differentiated cells and tissues from stem cells, activating somatic differentiated cells to produce transcripts from their genes, and transforming cells to acquire the capacity to produce specific products lost in degenerative diseases.

24. The method for regeneration of cells and tissues of claim 19, wherein resident cells in a degenerated region produce substances needed for physiological function of that area.

25. The method for regeneration of cells and tissues of claim 24, wherein said resident cells in a degenerated region contain specific target macromolecule structures for treating Parkinson's disease, and wherein cells of the basal ganglia produce dopamine and subsume functions of degenerated cells.

26. The method for regeneration of cells and tissues of claim 24, wherein said resident cells in a degenerated region contain specific target macromolecules for treating for Alzheimer's disease, wherein cells in the brain produce acetylcholine and subsume functions of degenerated cells.

27. The method for regeneration of cells and tissues of claim 24, wherein said resident cells in a degenerated region contain specific target macromolecule structures for treating stroke, wherein cells are induced to differentiate and replicate to replace ischemic cells.

* * * * *